United States Patent [19]
Coyne

[11] Patent Number: 6,017,757
[45] Date of Patent: Jan. 25, 2000

[54] ISOLATED VIABLE NEMATODE INTESTINAL CELLS

[75] Inventor: Cody P. Coyne, Starkeville, Miss.

[73] Assignee: Mississippi State University, Miss.

[21] Appl. No.: 08/804,136

[22] Filed: Feb. 20, 1997

[51] Int. Cl.⁷ ..................................................... C12P 5/06
[52] U.S. Cl. ........................ 435/325; 424/93.1; 424/93.7
[58] Field of Search ................. 424/93.1, 93.21, 424/93.7; 119/6, 7; 435/325, 347; 800/2

[56] References Cited

U.S. PATENT DOCUMENTS

| | | | |
|---|---|---|---|
| 4,447,537 | 5/1984 | Yunker et al. | 435/235 |
| 5,094,954 | 3/1992 | Previc | 435/242 |

FOREIGN PATENT DOCUMENTS

| | | | |
|---|---|---|---|
| WO86/03680 | 7/1986 | WIPO | A61K 39/00 |
| WO 90/11086 | 10/1990 | WIPO . | |
| WO94 06463 | 3/1994 | WIPO | A61K 39/00 |
| WO 95/12671 | 5/1995 | WIPO . | |
| WO/ 95/26402 | 10/1995 | WIPO . | |

OTHER PUBLICATIONS

Gordon et al., Can. J. Zool. (1990), 68(3), 511–16.
Franke et al., Science, (Jul. 8, 1983) 221 (4606) 161–3.
Hirumi et al., Phytopathology 59 (11). 1969.
Sanders et al., Nematologica 19 (4). 1973 567–568.
Rickard et al., In "In Vitro Methods for Parasite Cultivation", Academic Press, Taylor, A. E. R. and J. R. Baker (Ed.), 1987. 407–451.
Lewis et al., Methods Cell Biol. (1995), Volume Date 1995, 48, 3–29.
Gamble H. and Mansfield L., "Characterization of excretory–secretory products from larval stages of *Haemonchus contortus* cultured in vitro", *Veterinary Parasitology* 62:291–305, 1996.
Gamble et al., "Developmentally regulated zinc metalloproteinases from third–and fourth–stage larve of the ovine nematode *Haemonchus controtus,*" *J. Parasitol.* 82(2):197–202, 1996.
Manousis, T. and Ellar, D. J. "Establishment of two cells lines from the nematode *Meloidogyne incognita* (Tylenchida; Meloidogynidae)" In Vitro Cell Dev. Biol. 26:1105–1114, Nov. 1990.

Kurtti, T. J. and Munderloh, U. G. "Mosquito cell culture", *Advances in Cell Culture,* 3:259–302, 1984.

Hobbs et al. "Culture of Cells from Juvenile Worms of *Schistosoma Mansoni*", *J. Parasitol.* 79(6):913–921, 1993.

Jenkins et al. "*Fasciola hepatica* in vitro: increased susceptibility to fasciolicides in a defined serum–free medium", *Parasitology* 95:165–171, 1987.

Howell, M.J. An Approach to the Production of Helminth Antigens in vitro: The Formation of Hybrid Cells Between *Fasciola Hepatica* and a Rat Fibroblast Cell Line, *Int. J. Parasitol.* 11(3):235–242, 1981.

Primary Examiner—Irene Marx
Attorney, Agent, or Firm—Needle & Rosenberg, P.C.

[57] ABSTRACT

The present invention provides a homogenous population of parasite cells, wherein the cells are not mosquito cells, capable of prolonged culture in vitro. Fractions from the cells, both cellular and non-cellular are also provided. Further provided is a method of treating or preventing parasite involvement with an animal comprising administering immunogenic amounts of the parasite cells of the invention or fractions derived from the cells to the animal, thereby treating or preventing the parasite involvement with the animal. Further provided is a method of detecting the presence of a parasite in an animal, comprising contacting either the parasite cells or cell fractions of the invention or antibodies of the invention with either an antibody containing sample or an antigen containing sample from the animal and detecting the presence of binding of either the antibodies in the sample with the cells or fractions of the invention or the binding of the antigens in the sample with the antibodies of the invention, the presence of binding indicating the presence of a parasite in the animal. In addition, the invention provides a method of culturing parasite cell populations in vitro comprising culturing a parasite in parasite culture medium under conditions which allow for decomposition and/or degradation of the cuticle layer of the parasite such that cellular buds are produced; disrupting the culture to cause the cellular buds to shear from the cuticle layer; and culturing the parasite cellular buds in cell culture medium. Finally provided is a population of differentiated nematode cells capable of prolonged culture in vitro.

9 Claims, 1 Drawing Sheet

ISOLATED VIABLE NEMATODE INTESTINAL CELLS

BACKGROUND OF THE INVENTION

1. Field of the Invention

The present invention relates to isolated viable parasite cells and to uses thereof. In particular, the present invention relates to vaccines for prevention or treatment of parasitic infestation or infection utilizing immunogenic material derived from isolated viable parasite cells.

2. Background Art

Parasite infections are widespread in the equine and livestock production industries. Losses attributed to parasitism are estimated in the hundreds of millions of dollars (Gibbs and Herd, 1986). Parasitism may manifest as either a clinical or subclinical condition. Although clinical parasitism may appear in a more dramatic fashion, subclinical parasitism is more pervasive, causing declines in feed efficiency, reproductive function and susceptibility to disease. These effects are complicated by the age of the animal, types of parasites present, nutritional and environmental stresses, management systems, presence of other disease conditions, genetic histories and numerous other factors (Gibbs and Herd, 1986; Hawkins, 1993).

Control of parasitism in the United States has centered on the use of anthelmintics, with literally billions of dollars spent annually on the administration of such products (Lanusse and Prichard, 1993). Traditionally, control has been therapeutic and curative in nature; animals are treated to prevent death rather than infection. Serious disease and mortality is decreased, but subclinical losses between treatments persist as a result of reinfection from contaminated pastures or stalling areas.

More recently, a more preventative approach to nematode control has become popular, depending on either strategic treatment with anthelmintics alone, or in combination with grazing/pasture management practices (Williams, 1986; Miller, 1993; Stromberg and Corwin, 1993). Rather than concentrating on adult parasites, the aim of these programs has been to decrease pasture contamination with infective larvae, thereby reducing the risk of parasite exposure. This in turn reduces the effects of subclinical parasitism within a livestock herd. Although anthelmintics afford many economic advantages, their use carries some distinct disadvantages; notably development of resistance and the potential hazards of persistent residues and ecotoxicity (Waller, 1993).

Complicating the efficacy of anthelmintics is the development of resistance, which has been well documented in ruminants. It was first reported in 1957 when *Haemonchus contortus* was found to be resistant to phenothiazine (Drudge, 1957). Resistance continues to be a problem even with the newer classes of anthelmintics. Although it is primarily a problem in horses and small ruminants, some resistance has also been reported in cattle parasites. Resistance of Ostertagia to levamisole (Lyons, 1981; Geerts, 1987; Williams, 1991; Williams, 1991) and to sustained release boluses of morantel (Borgsteede 1988), with side-resistance to levamisole (Borgsteede 1991), and resistance of *Trichostrongylus axei* and *Cooperia oncophora* to oxfendbendazole (Eagleson & Bowie, 1986; Jackson, 1987) have been documented. Anthelmintic resistance occurs with all classes of drugs used to control nematodes. Cross-resistance, multiple resistance and side resistance have been reported (Craig, 1993). Development of resistance is believed to be encouraged by rapid "rotation" between different preparations. Reversion or selection away from resistance, once the selection pressure is removed, is slow (Kelly & Hall, 1979).

Development of vaccines against gastrointestinal parasites of cattle has in general produced less than optimal results. Because ruminant gastrointestinal nematodes thrive irrespective of the immune system, a vaccine mimicking this immunological equilibrium is unlikely to be of high efficacy. Vaccines capable of inducing protection via a mechanism different from that mimicking natural immunity would theoretically be more successful (Willadsen, 1993).

Because of their physical location, "concealed" antigens from gut tissue are not normally exposed or "visible" to the host's immune system and therefore do not normally elicit an immune response. Vaccination of the host with isolated preparations of "concealed" antigens from various parasites has shown some potential in inducing a lethal immune response.

Gut tissue from the Anopheles mosquito was first used as a source of antigen for the production of a vaccine. Mosquitoes that took blood meals from rabbits injected with homogenates of heterologous cell fractions from mosquito midgut had a higher death rate than those fed on control rabbits (Alger & Cabrera, 1972). Cattle and guinea pigs were immunized with homogenates of heterologous cell fractions containing antigens extracted from the gut of partially fed *Dermacentor andersoni* ticks. Engorgement and egg production were significantly reduced in ticks that fed on vaccinated animals (Allen & Humphreys, 1979). Similar success was achieved with calves vaccinated with *Amblyomma americanum* (McGowan, 1981). These successes and the emergence of acaricide-resistant strains of ticks encouraged work on the cattle specific tick, *Boophilus microplus*.

Immunization of cattle with crude extract of partially fed ticks decreased tick populations (Johnston, 1986). This protection was different from the naturally acquired resistance that involves a hypersensitivity reaction at the site of tick attachment, which is a reaction not present in the response to immunization (Kemp, 1986). Histopathology of gut tissue from ticks fed on immunized cattle showed damage not evident in ticks fed on cattle with natural tick infestations (Agbede & Kemp, 1986). In addition, cattle injected with crude tick gut membrane and adjuvant had significantly higher antibody levels than naturally infested cattle. Cattle vaccinated with crude gut membrane antigen and then challenged with parasites did not display any obvious anamnestic response, although the challenge dosage was sufficient to produce a significant, but low antibody response in naive animals (Opdebeeck & Daly, 1990). These observations support the contention that vaccination with gut membrane and natural tick infestation do not invoke the same immune response.

Experiments done with purified crude tick extract demonstrated that the immunoprotective antigen was associated with parasite gut membrane (Opdebeeck, 1988; Willadsen, 1988; Willadsen, 1989). Further characterization of the antigen revealed it to be a membrane-bound glycoprotein referred to as Bm86. Immunization of host animals with this antigen decreased tick survival, engorgement weights and fecundity. Antibody to this antigen rapidly inhibited the endocytotic activity of parasite digestive cells (large lumen side gut cells separated from the basement membrane) in the tick gut. This antigen was cloned and expressed as inclusion bodies in *E. coli*. Ticks fed on cattle vaccinated with these inclusion bodies were significantly damaged, but not killed (Rand, 1989).

Monoclonal antibodies, produced against *Boophilus microplus* midgut membrane precipitated antigens, were >99% protective in challenge studies. These antigens separated into one major and five minor bands upon the application of conventional SDS-PAGE, indicating that the epitope recognized by the monoclonal antibody is repeated on several antigens. These antigens are thought to be different from Bm86 because vaccination with these antigens results in tick death (Lee & Opdebeeck, 1991).

Antigens may be common to more than one stage of the parasite life-cycle and the shared reactive epitopes may occur on different proteins in the different stages (Maizels, 1987). Because antibody levels have been correlated to the level of protection provided by immunization with tick gut antigen (Opdebeeck, 1988; Lee & Opdebeeck, 1991), larval and adult antigen extracts were purified using anti-gut antibodies. Protection provided by both larval and adult purified antigens was greater than 80%, thus the protective antigens may be common to both stages. Extracts from tick egg membrane were found to be immunogenic, but not protective, to challenge infections. Anti-egg membrane and anti-gut membrane antibodies were cross reactive, recognizing common antigens for the egg and tick gut (Kimaro, 1993).

Because anti-tick antibodies in the sera of cattle vaccinated with tick gut membrane and of cattle naturally infested with ticks reacted with adult tick salivary gland and gut antigens as well as with larval antigens, it was thought that *Boophilus microplus* gut antigens were not truly "concealed" antigens (Opdebeeck & Daly, 1990). It was determined, however, that when antisera from naturally infested cattle reacted with Bm86, it was through a cross-reactive carbohydrate epitope which had no deleterious effect on ticks (Willadsen & McKenna, 1991). Thus, the gut antigen Bm86 is "concealed" and its polypeptide epitopes are responsible for providing immunoprotection.

"Concealed" antigens have also been proposed as a means of controlling cat flea infestations involving species of *Ctenocephalides feli*. Imunoglobulins produced in rabbits immunized with homogenates of cell fractions containing antigens from the midgut of fleas were fed to cat fleas and shown to have harmful effects. Dogs immunized with crude antigens and challenged with fleas had fewer surviving fleas than did control animals and surviving females laid fewer eggs (Heath, 1994).

Species of *Haemonchus contortus,* an economically important blood feeding nematode in sheep, has also been the target of vaccine development. Nonspecific immune responses induced by injections of Freund's complete adjuvant provided some protection against *Haemonchus contortus* (Bautista-Garfias, 1991). Vaccination with cuticular collagen was not protective although it was immunogenic (Boisvenue, 1991). In contrast, soluble antigens from adults and third stage larvae proved to be poor immunogens (Cuquerella, 1991).

Contortin is an extracellular, polymeric protein which is loosely associated with the lumenal surface of the nematode gut epithelium plasma membrane. Vaccination with a contortin-rich extract prepared from whole worm homogenates is protective in young lambs. Nematode populations in vaccinated animals are smaller in numbers than those found in control animals (Munn, 1987). Serum antibodies precipitated several components of the contortin-rich extract.

Vaccination with crude extracts of gut tissue from adult nematodes and third stage (L3) larvae provided similar protection in goats (Jasmer & McGuire, 1991). Reductions both in numbers of worms and in egg output were achieved in the immunized group. Antibodies from immune serum recognized seven gut proteins, some of which were integral membrane proteins. This antigen preparation may contain a significant amount of contortin (Munn, 1993b). Immunohistochemistry provided confirmation that the antigen originated from parasite intestinal cell populations and demonstrated cross-reactivity with microvillar proteins in *Ostertagia ostertagi* and several equine small strongyles. Reduction in the number of nematodes recovered after immunization with *Haemonchus contortus* gut extract was confirmed by Smith (1993) in young Suffolk lambs. Serum from sheep exhibiting natural immunity to *Haemonchus contortus* did not react with the gut membrane proteins, confirming the "concealed" nature of these proteins. Passive transfer with immune serum from vaccinated sheep decreased egg output in recipient animals. The presence of host antibody coating the microvilli of nematodes recovered from these animals suggested antibody as the effector mechanism. No lesions were observed in the gut membranes. Coating of the microvilli may neutralize necessary proteins (i.e. enzymes) resulting in the death of the worm, or the coating may mechanically block nutrient absorption, effectively starving the nematode.

Antigen H11, present in both fourth (L4) and fifth-stage (L5) larvae of *Haemonchus contortus*, is the major microvillar integral membrane protein of *Haemonchus contortus*. Vaccination of young Merino lambs with H11 and with an H11 enriched preparation (containing a small amount of peripheral membrane protein, P1) resulted in a reduction in mean number of nematodes and nematode egg output. Late onset of egg production was noted, suggesting that the effector mechanism may act on pre-adult stages of the parasite (Munn, 1993a). Reductions in numbers of worms and egg output correlated with the serum antibody titer to H11 (Smith, 1993; Tavernor, 1992a,b). The enzymatic nature of H11 has been deduced from DNA sequencing and confirmed by assay and specific inhibitor studies (Munn, 1993). The activity of H11 is inhibited by serum antibodies from vaccinated animals. Most of the antibodies produced are targeted at H11 (Munn, 1993) and levels of inhibition correlate with levels of protection (Munn, 1993). Like contortin, host immunoglobulin appears to be the effector mechanism. Host antibody binds to the parasite intestine as early as seven days post-infection, with lethality observed in nematodes between days 7 and 14. Larvae younger than day 7 post-infection are apparently not susceptible to the immune response. Antigen H11 immunized lambs challenged with trickle inoculations were largely protected against the anemia and egg output observed in challenge controls. They grew as efficiently as the uninfected controls and acquired natural immunity during the course of the trickle infection. Animals challenged with either benzimidazole-resistant or susceptible strains of *Haemonchus contortus* were equally protected by H11 vaccination (Smith & Smith, 1993). Female parasites were lost more quickly than males, accounting for the reduction in egg output.

Vaccination with fractions of the whole worm H11 enriched extract showed the protective activity to be associated primarily with H11. Another fraction, P1 or H45 was also protective but in much greater amounts than H11. Immunization with H11 enriched extract (containing P1 ) conferred protection in Dorset lambs and Clun Forest sheep (Tavernor, 1992a; Munn, 1993b), but greater nematode reduction was observed in Clun Forest sheep. This difference in protection could be due to breed, quantity of antigen, or age of lambs. In a direct comparison of the protection conferred by vaccination with H11 enriched contortin-free antigen (Munn, 1993b) and by vaccination with contortin-enriched antigen (Munn, 1987), the mean protection (i.e. worm number and egg production declines) achieved with the H11 enriched contortin-free preparations was equal to the best protection achieved with the contortin-enriched preparations, even though lesser amounts of H11 protein were used. Thus, H11 is more effective than contortin. Sufficient protection was achieved with immunization using 100 mg of H11 antigen and greater protection was not demonstrated with larger doses of antigens (Tavernor, 1992a). Vaccination with 95% pure H11 reduced the number of nematodes up to 93% with a 94.6% reduction in egg production.

Cross protection was not demonstrated in challenge studies with *Ostertagia circumcincta* and *Nematodirus battus*. This may be a reflection of antigenic difference or because nematode ingestion of host imunoglobulin was in amounts insufficient to promote lethal injury (Smith, 1993). Monoclonal antibodies made against gut surface epitopes of *Haemonchus contortus* identified epitopes also located in the body wall, the region of the cuticle and on internal organs of third-stage (L3) larvae as well as in the gut and tissues of *Ostertagia ostertagi, Trichostrongylus colubriformis*, equine small strongyles and *Caenorhabditis elegans* (Jasmer, 1992).

Another protective component was isolated from the integral membrane fraction of intestinal cells using lectins as ligands to purify the microvillar glycoproteins from whole worm extracts. This fraction, Haemonchus galactose containing glycoprotein complex or H-gal-GP is readily separated from H11 or P1 by SDS-PAGE, its lectin binding specificity and its lower isoelectric point. In a side by side comparison study, H-gal-GP was less protective than H11 and reductions in numbers of nematodes were not as great as for H11, although reductions in egg production were similar. Like H11, H-gal-GP is more effective against female worms than male worms. Comparisons in the literature show H-gal-GP to be more effective than the H45 complex. Differences in protection induced by H-gal-GP and H45 may be due to the specific immunization protocol used.

The establishment of a heterogenous cell line from a plant parasite (caterpillar stage) has been described (Manousis & Ellar, 1990). These authors stated that this was the first time such a technique had successfully been performed with a nematode. Heterogenous (non-specific) cell populations survived for no longer than three months. Supplementation of growth medium with fetal bovine serum (FBS, 10% v/v) supported propagation of cell populations for a period of just greater than five months. Kurti et al. (1988) describe the propagation of heterogenous cell lines derived from tick (*Dermacentor variabilis, Rhipicephalus appendiculatus, Rhipicephalus sanguineus,* and *Boophilus microplus*) embryos in growth medium containing 10% FBS, although there was no attempt to propagate a specific cell line through selective laboratory techniques. In another description of parasite cell line propagation, whole parasites were homogenized as staring material, so no attempt was made to selectively cultivate a specific cell line (Hobbs et al., 1993). Parasite homogenate was transferred to wells of a tissue culture plate containing a buffalo rat liver "feeder" cell layer and serum "free" growth medium was utilized. Modification of a DMEM-like growth medium to contain less KC1 and glucose allowed maintenance of viable cell lines for four weeks or longer. Planting of juvenile worm cells on a feeder layer of irradiated buffalo rat liver (BRL) cells extended the viability of cell clusters from a few weeks to as long as six months. Feeder layers of bovine endothelial or mouse embryo (3T3) cells were less effective. Kurtti and Munderloh (1984) described production of mosquito cell culture from larval tissues, adult ovary and embryonic tissues, resulting in the cultivation of heterogenous mixtures of mosquito cells for several years. Munderloh et al. (1994) describe the propagation of heterogenous cell populations from embryonated tick eggs. These investigators described difficulty in preserving the cells in liquid nitrogen for long periods of time. Cells were propagated in tissue culture growth medium containing fetal bovine serum (FBS 20% v/v). The time interval between initiation of the primary culture and the first subculture ranged from 6 to 12 months.

As can be seen from the studies described above, antigens expressed by parasite cells have shown potential in providing protective immunity in sheep and cattle. Unfortunately, these fractions were derived from parasite intestinal tracts which have been harvested manually by microdissection. Thus, it is very labor intensive and expensive to obtain sufficient amounts of immunogenic proteins. Further, it is difficult to obtain sufficient purity of antigens and to identify antigens that may be useful in vaccines. Cell lines which have been established from parasites have been heterogenous and undifferentiated populations which have been difficult to sustain in a tissue culture environment for extended periods of time. Thus, a need exists for homogenous populations of parasite cells that can be sustained in culture for prolonged periods of time.

The present invention fulfills this need by providing homogenous populations of parasite cells which are sustainable in culture for prolonged periods of time and methods for producing such homogenous populations.

SUMMARY OF THE INVENTION

The present invention provides a homogenous population of parasite cells, wherein the cells are not mosquito cells, capable of prolonged culture in vitro. Fractions from the cells, both cellular and non-cellular are also provided. Also provided are antibodies which specifically bind to the cells or cell subfractions and anti-idiotype antibodies.

Also provided is a method of treating or preventing parasite involvement with an animal comprising administering immunogenic amounts of the parasite cells of the invention or fractions derived from the cells to the animal, thereby treating or preventing the parasite involvement with the animal.

The invention also provides a method of screening a compound for anthelmintic activity comprising contacting the compound with the cells of the invention and determining whether the compound has a detrimental effect on the cells.

Further provided is a method of detecting the presence of a parasite in an animal, comprising contacting the parasite cells of the invention or fractions derived from the cells with an antibody containing sample from the animal and detecting the presence of binding of the antibodies in the sample with the cells or fractions, the presence of binding indicating the presence of a parasite in the animal.

In addition, a method for detecting the presence of a parasite in an animal is provided, comprising contacting antibodies of the invention with a sample from the animal potentially containing parasite antigens and detecting the presence of binding of the antibodies with an antigen, the presence of binding indicating the presence of a parasite in the animal.

Furthermore, the invention provides a method of culturing parasite cell populations in vitro comprising culturing a parasite in parasite culture medium under conditions which allow for decomposition and/or degradation of the cuticle layer of the parasite such that cellular buds are produced; disrupting the culture to cause the cellular buds to shear from the cuticle layer; and culturing the parasite cellular buds in cell culture medium.

The present invention also provides a population of parasite cells, not including mosquito cells, capable of prolonged culture in vitro, produced by the method of culturing parasite cell populations in vitro comprising culturing a parasite in parasite culture medium under conditions which allow for decomposition and/or degradation of the cuticle layer of the parasite such that cellular buds are produced; disrupting the culture to cause the cellular buds to shear from the cuticle layer; and culturing the parasite cellular buds in cell culture medium.

Finally, the present invention provides a population of differentiated nematode cells capable of prolonged culture in vitro.

Various other objectives and advantages of the present invention will become apparent from the following description.

DETAILED DESCRIPTION OF THE INVENTION

Figure 1A:
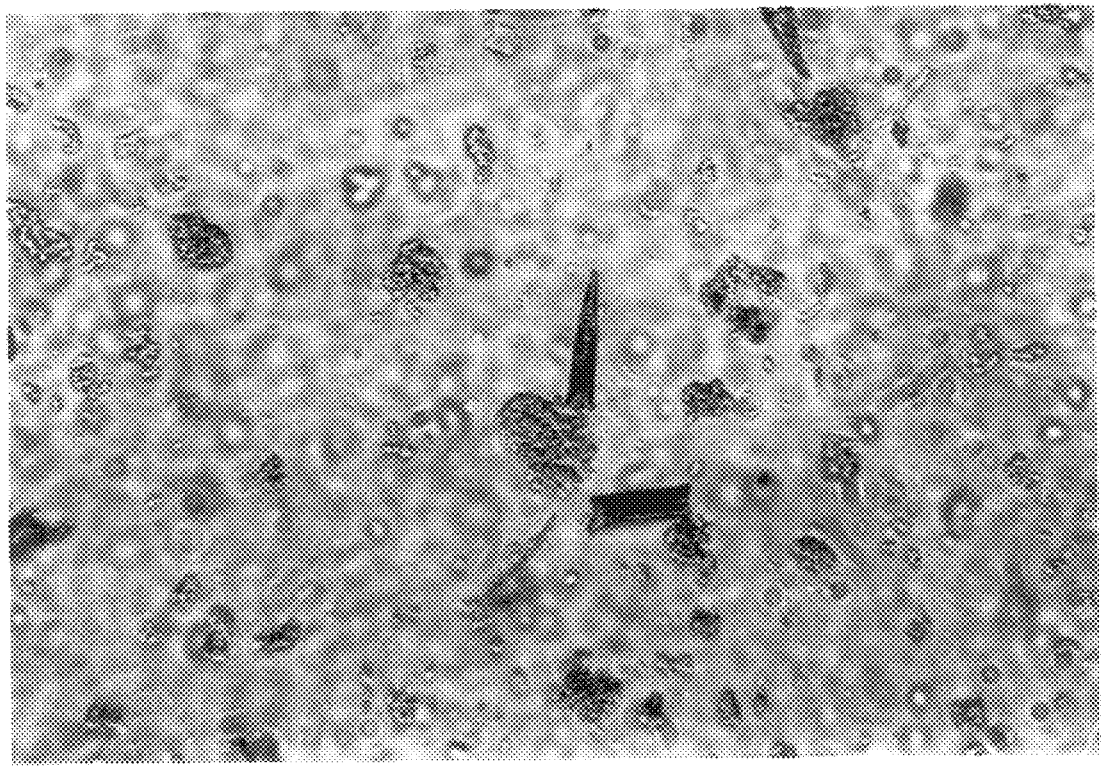
FIG. 1 shows parasite cells propagated in a tissue culture (in vitro) environment. A: Clusters represent parasite cellular buds which have been extruded from the cuticular sheaths of larvae. B. Cellular clusters are of a larger diameter than individual larvae, indicating in vitro proliferation of the cellular buds after extrusion from larvae.
Figure 1B:
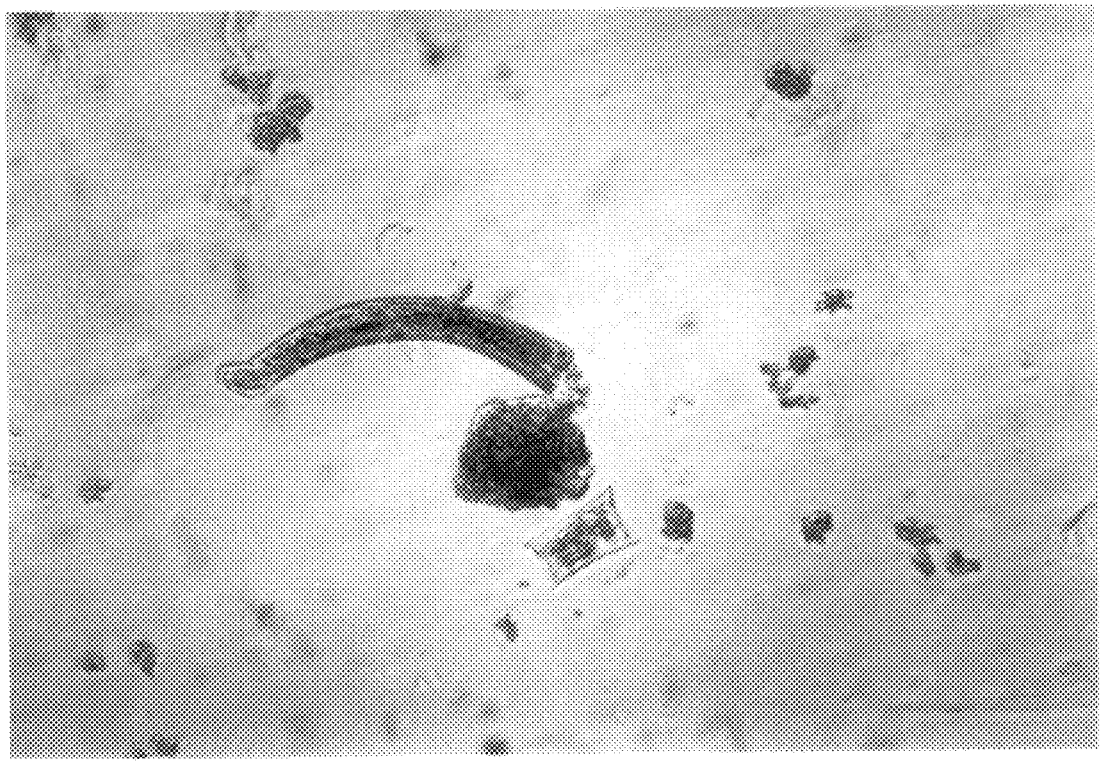

The present invention is more particularly described in the following examples, which are intended as illustrative only since numerous modifications and variations therein will be apparent to those skilled in the art. As used in the claims, "a" can include multiples.

This invention provides a homogenous population of parasite cells, which are not mosquito cells, capable of prolonged culture in vitro. By "homogenous" is meant that the cells are substantially only of one type. For example, the homogenous population can consist of any number in the range between 100 and 80% of cells of one type, such as 100%, >95%, >90%, >85%, >80%, 79% and in the preferred range, especially 90%, 91%, 92%, 93%, 94%, 95%, 96%, 97%, 98%, 99% and 100%. The percentage of cells of one cell type in the homogenous population can be determined by methods standard in the art, such as for example, fluorescence activated cell sorting (Harlow and Lane, 1988). By "capable of prolonged culture" is meant that the cells can be passaged and frozen and reconstituted such that the cells can be maintained as a homogenous population for an indefinite time period. For example, the cells of the present invention have been maintained as a homogenous population of cells for over three years.

Because these cells are maintained as a suspension culture, these cells are best passaged when the bottom of the tissue culture flask can be observed to contain a substantial amount of cellular sediment. The cells of this invention can be passaged either by "splitting" the cells in one culture flask into additional tissue culture flasks or adding additional cell culture medium to the existing flask. Additionally, the cells of the present invention can be frozen for long term storage as viable cells according to standard protocols known in the art for the cryopreservation of cultured cells. For example, medium containing cells can be centrifuged to pellet the cells and the supernatant medium can be discarded. The cell pellet can then be resuspended in freeze medium (e.g., IPL-41 or SF-900 medium or a 50/50 mixture of IPL-41 and SF-900) containing, for example, 10% (v/v) DMSO and supplemented with amikacin (2.5 mg/ml) and oxacillin (2.5 mg/ml). The medium and cells are then transferred to cryovials and placed at −96° C. for one hour. The cryovials are then placed into and continuously maintained in liquid nitrogen until reconstituted.

To reconstitute the cells, for example, cryovials containing cells are removed from liquid nitrogen and the outside of the vial is sterilized with alcohol. The cells are thawed by placing the vial in a water bath at room temperature (RT; 25°). Two ml of cell culture medium are added to the vial to dilute the DMSO and the cells are pelleted at low speed (200–300×g). The supernatant is decanted and fresh medium is added and the cells are pelleted again. The supernatant is again decanted and the cells are resuspended in tissue culture medium which is about 90% fresh medium and 10% spent medium and transferred to a tissue culture flask. Cell populations cultured from larvae or reconstituted after cryopreservation can be passaged an unlimited number of times and can be maintained as viable cells indefinitely (i.e., for a period of years).

The parasite cells derived or used in this invention can be of any cell type found in the adult or larval parasite. For example, such cells can include, but are not limited to, intestinal esophageal secretory, muscular, neurological and reproductive cells, such as uterine cells. Especially useful for treatment and prevention of parasite involvement are intestinal cells.

As described in more detail below, the cells can be used, for example, for treatment, prevention and diagnostic purposes. For any of these purposes, the cells can either be used intact, partially or completely lysed, as well as with or without the culture medium in which the cells are being cultured. Thus, different cellular fractions can be derived from the parasite cells. For example, membrane associated antigens can be separated from the rest of the culture and cellular components as membrane fractions and used for various purposes. Other cellular fractions can include but are not limited to, whole cell fractions, subcellular organelle fractions, enzyme fractions, genetic material (e.g., RNA, DNA), etc. In addition, the medium in which the cells are cultured can be used without the cells, as certain cellular components of the cells will have been released into the medium which can be harvested and analyzed as noncellular fractions. The medium with and without the cells and/or the cells, lysed or unlysed, can be used in therapeutic, prophylactic or diagnostic assays to best optimize the ratio of cells to medium and the ratio of lysed to unlysed cells. Opimization would involve conducting in vitro and/or in vivo efficacy trials according to protocols standard in the art, to determine or identify those medium:cell ratios and lysed cell:unlysed cell ratios capable of producing optimal therapeutic, prophylactic or diagnostic results (e.g., Smith, 1993).

The cells of the invention can be lysed by any means standard in the art such as detergent solubilization and mechanical disruption (Travenor et al., 1992). Various cell fractions can be separated from the cell lysate by standard cell fractionation techniques, such as, for example, gel filtration chromatography; ion exchange chromatography, affinity chromatography, high pressure liquid chromatography (HPLC) and the like, as are well known in the art (e.g., Travenor et al., 1992; Munn et al., 1993; McKerrow et al., 1990; Gambel et al., 1990).

Alternatively, a protein fraction of the parasite cells can be obtained by treating the cells with an ionic detergent such as sodium dodecyl sulfate or a nonionic detergent such as Triton X-100 ($C_{34}H_6O_{11}$ average) or ethylphenyl-polyethylene glycol (NP40, Shell Oil Company). The protein fractions so obtained can be tested for immunogenicity, specificity and biochemical enzyme activity as described above. Other immunogenically specific determinants of the parasite cells can be obtained by the standard methods, for example, as described above.

Proteins and protein fragments produced by the cells of this invention can be isolated and purified and the amino acid sequence and nucleic acid sequence of these proteins and protein fragments can be determined according to methods standard in the art. The nucleic acids encoding the proteins and protein fragments can be cloned into vectors and expressed in cells and/or transgenic animals according to molecular genetic protocols well known to the artisan (see e.g., Sambrook et al., 1989).

Other components can be added to the lysed or unlysed cells, cellular fractions derived from the cells or medium removed from the cell cultures. Thus, the invention provides compositions comprising these components and can include an effective amount of the cells, fractions thereof or noncellular fractions, in combination with a pharmaceutically acceptable carrier and, in addition, may include other medicinal agents, pharmaceutical agents, carriers, adjuvants, diluents, etc. By "pharmaceutically acceptable" is meant a material that is not biologically or otherwise undesirable, i.e., the material may be administered to an individual along with the selected compound without causing any substantial undesirable biological effects or interacting in a deleterious manner with any of the other components of the pharmaceutical composition in which it is contained. Actual methods of preparing dosage forms are known, or will be apparent, to those skilled in this art (see, e.g., Martin, latest edition; Arnon, 1987). The carrier would naturally be selected to minimize any degradation of the active ingredient and to minimize any adverse side effects in the subject.

In another embodiment, the composition could include an adjuvant to enhance the therapeutic or prophylactic effect of the active ingredient. The adjuvant can be selected by standard criteria based on the particular antigen used, the mode of administration and the subject (Arnon, 1987). For example, the composition can include Freund's complete adjuvant, Freund's incomplete adjuvant, aluminum hydroxide or any other adjuvant known to enhance the immunogenicity of an antigen.

Examples of parasites which can be used to generate the homogenous populations of parasite cells of the present invention can include, but are not limited to, nematodes, trematodes, helminths annelids and cestodes, as well as arthropod and arachnid species (e.g., ticks, mites, lice and fleas). A particularly useful homogenous parasite cell line is derived from a nematode. Examples of nematodes useful in the present invention can include, but are not limited to, Cooperia, Oesophagostomum, Ostertagia, Haemonchus, *Dirofilaria immitis* and Dictyocaulus. Economically significant parasites that can be employed in the present invention can include, for example, *Cooperia bisonis, Cooperia cuticei, Cooperia mcmasteri, Cooperia oncophora, Cooperia pectinata, Cooperia punctata, Cooperia spatulata, Cooperia surnabada, Dictyocaulus viviparus, Haemonchus contortus, Haemonchus placei, Haemonchus similis, Oesophogostomum radiatum, Ostertagia bisonis, Ostertagia orloffi, Ostertagia ostertagi, Trichostrongylus axei, Trichostrongylus colubriformis, Trichostrongylus longispicularis, Fasciola magnum, Fasciola hepatica, Amblyomma americanum, Amblyomma cajennense, Amblyomma maculatum, Boophilus annulatus, Dermacentor albopictus, Dermacentor andersoni, Dermacentor occidentalis, Dermacentor variabilis, Ixodes cookei, Ixodes pacificus, Ixodes scapularis, Chorioptes bovis, Psorergates bos, Psoroptes ovis, Sarcoptes scabei, Oesophogostomum columbianum, Oesophogostomum venulosum, Ostertagia circumcincta, Ostertagia occidentalis, Ostertagia trifurcata, Trichostrongylus capricola, Nematodirella longispiculata, Nematodirus abnormalis, Nematodirus davitiani, Nematodirus filicollis, Nematodirus helvetianus, Nematodirus lanceolatus, Nematodirus spathiger, Ascaris suum, Hyostrongylus rubidus, Oesophagostomum brevicaudum, Oesophagostomum dentatum, Oesophagostromum georgianum, Oesophagostonum quadrispinulatum, Strongyloides ransomi, Strongyloides westeri, Trichuris suis, Strongylus edentatus, Strongylus equinus, Strongylus vulgaris, Strongylus westeri, Dirofilaria immitus* and *Ascaris canis*.

The invention also provides an antibody or ligand which specifically binds the parasite cells or fractions of the cells of the present invention. As used herein, antibodies can include immunoreactive antibody fragments. These antibodies can be made by standard techniques well known in the art (see. e.g., Harlow & Lane, 1988). Monoclonal or polyclonal antibodies raised against antigens (e.g., derived from the present intact cells or from cell fractions purified from cell lysates) can be used as diagnostic reagents to detect antigens in tissue or body fluids of an animal, as well as to purify parasite antigens through the use of affinity-capture and other antigen purification techniques. The antibodies of this invention can also be used in therapeutic applications to treat or prevent parasite involvement with an animal.

Antibodies can either be purified directly from an immunized animal, or antibody-producing spleen cells can be obtained from the animal for hybridoma production. The spleen cells are fused with an immortal cell line and maintained as hybridomas for antibody secretion. Likewise, purified polyclonal antibodies specifically reactive with the antigen are within the scope of the present invention. The polyclonal antibodies can be obtained by standard immunization and purification protocols (Harlow and Lane, 1988).

Detecting the reaction of the ligand or antibody with antigen can be facilitated by the use of a ligand or antibody that is bound to a detectable moiety. Such a detectable moiety will allow visual detection of a precipitate or a color change, visual detection by microscopy, or automated detection by spectrophotometry, radiometric measurement or the like. Examples of detectable moieties include fluorescein and rhodamine (for fluorescence microscopy), horseradish peroxidase (for either light microscopy or electron microscopy and biochemical detection), biotin-streptavidin (for light or electron microscopy) and alkaline phosphatase (for biochemical detection by color change). The detection method and detectable moiety used can be selected from the list above or from other suitable examples according to standard criteria applied to such selections (Harlow and Lane, 1988).

An anti-idiotype antibody which specifically binds the antibodies is also provided. Such an anti-idiotype antibody could naturally be used as an immunogen to provide therapeutic or prophylactic effect against a parasite. Anti-idiotype antibodies represent the image of the original antigen and can function in a vaccine preparation to induce an immune response to a pathogenic antigen, thereby avoiding immunization with the pathogen or the pathogenic antigen itself (Harlow & Lane, 1988).

The invention also provides a method of treating or preventing parasite involvement with an animal, including humans, comprising administering immunogenic amounts of the parasite cells or fractions derived from the parasite cells to the animal, thereby treating or preventing the parasite involvement of the animal. By "parasite involvement with an animal" is meant any interaction or connection between a parasite and an animal by which the parasite infects or infests an animal, attaches to the animal or takes a blood or other tissue or body fluid meal from the animal, whether the animal is alive or dead.

The parasite cells, fractions of the cells or non-cellular fractions can be tested for immunogenicity by methods known in the art (Harlow & Lane, 1988, Arnon, 1987). Briefly, various concentrations of potentially inmunogenic cells or specific cell fractions are prepared and administered to the animal in various concentrations and the immunological response (e.g., the production of antibodies or cell mediated immunity) of the animal to each concentration is determined by standard protocols. The amount and type of immunogen administered will depend upon the species, size and condition of the animal. Thereafter, an animal so inoculated with the immunogen can be exposed to the parasite to test the potential vaccine effect of the specific immunogen. The specificity of the potential immunogen can be stained by testing sera and other fluids, as well as lymphocytes from the inoculated animal, for cross-reactivity with other closely related parasites. Once the immunogenicity is established, the amount of immunogen to be administered to a particular animal can be optimised according to standard procedure as known in the art (Harlow & Lane, 1988, Arnon, 1987).

In a preferred embodiment, the immunogen can comprise a "hidden antigen" which is an antigen produced by the parasite which is located on or within the parasite in such an anatomical location that, under typical circumstances of parasite involvement with an animal including human, the animal's immune system does not have direct access with the antigen (e.g., antigens expressed on parasite intestinal cells). If the animal is effectively challenged with an immunogen which is a "hidden antigen" of a parasite, it is possible to induce a cellular and/or humoral immune response in the animal that is therapeutic or protective against the immunogen and thus against the parasite. For example, if an antigen from a parasite intestinal cell is appropriately presented to the animal and a humoral and/or cellular immune response is induced, the subsequent ingestion of parasites having the antigen can promote a lethal event for the parasite, through either a direct cytotoxic effect on the parasite or interference with the nutrient absorptive properties of the parasite's intestinal tract due to antibody binding, or a combination of both mechanisms.

Also in a preferred embodiment, the immunogens or antigens of the present invention are cross reactive with immunogens or antigens of different species of parasites; i.e., these antigens or immunogens are "shared" among different parasite species. Such shared antigens or immunogens can be identified as being immunologically cross reactive with antigens or immunogens from other species according to serological protocols standard in the art for identifying cross reactive antigens. The antibodies employed in these cross reactive studies can be produced according to the methods described herein. Antigens can be selected for determination of their immunological cross reactive capabilities on the basis of similarities in molecular weight, Con-A binding affinity, enzyme activity, etc. according to the methods provided herein.

The mode of administration of the immunogen can vary depending upon the species, size and condition of the animal. The therapeutic or prophylactic immunogen of the invention is typically administered parenterally, either subcutaneously or intramuscularly by injection. Of course, the immunogenic amount can be given in divided doses or administered at multiple sites in the animal. For example, the immunogen can be administered in a single dose or in two doses at various intervals (e.g., one, two or four weeks). Booster immunizations can also be given at various intervals (e.g., bi-weekly intervals) as needed to maintain the therapeutic or prophylactic effect desired. Immunizations can also be administered to subjects as "trickle inoculations," such as, for example, by administering about 50–100 μg of immunogen to a subject either subcutaneously or intramuscularly every other day for a period of 14–30 days.

Parenteral administration is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of immunogen is maintained. See, e.g., U.S. Pat. No. 3,710,795.

The animal can be any animal in which there is a potential or existing need to treat or prevent parasite involvement. Typical animals can be selected from the group consisting of: for example, human, bovine, equine, porcine, caprine, ovine, canine, feline, and avian species. Relatedly, the animal could be of a wild animal species in which it is desirable to control parasites, for example, in zoological settings where wild animals are maintained and/or in situations where parasites could be passed from a wild animal to a domestic animal or human.

The invention also provides a method of treating or preventing parasite involvement with an animal comprising administering to the animal antibodies of the invention. Relatedly, the invention provides a method of treating or preventing parasite involvement with an animal comprising administering to the animal anti-idiotype antibodies to the antibodies of the invention. Specifically, whole cells or antigenic fractions can be harvested from the parasite cell populations of the present invention and subsequently purified according to the methods provided herein. These antigens can be used in the production of monoclonal antibodies according to well known protocols for producing antibody secreting hybridomas, as well as for generating polyclonal antibodies by immunizing animals (e.g., mice, rabbits) with the antigens and purifying the resultant antibodies from the animal's serum by well known protocols such as affinity chromatography. These antibodies can then be used as a source of secondary antigen to produce anti-idiotype antibodies according to the same protocols described herein.

The invention further provides a method of screening a compound for anthelmintic activity comprising contacting the compound with the cells of the invention and determining whether the compound has a detrimental effect on the cells. The only requirement for a successful screen of compounds is that a quantifiable number of cells from the homogenous parasite cell culture be viable such that the number of cells that are affected by the compound can be determined. Thus, the composition can further comprise cells not from the homogenous parasite cell population. "Detrimental effect" as used herein can include any effect which can be observed which is known to be atypical of physiologically normal cells in tissue culture such as, for example, a change in the condition or appearance of the parasite cells which is pathological (e.g., cytopathology, syncytia formation, altered biochemical function, failure to produce or express antigens, adherence or non-adherence to tissue culture substrate, rounding or flattening of cells, disruption of a monolayer, abnormal clumping of cells, growth in multiple layers, abnormal cellular inclusions, etc.) or parasite cell death.

In the screening method, the compound can be an antibody or other molecule, including synthetic, organic or naturally produced molecules (Baron et al., 1989; DeClercq, 1989). Such organic molecules can have active site-directed properties that inhibit parasites in vitro or in vivo. Additionally, any molecule that interferes with any phase of the parasite life cycle can be identified and screened according to the present methods.

The compound can be screened by contacting various concentrations of the compound of interest with the cells of the present invention. The concentrations can be selected empirically or can be extrapolated from teachings in the art regarding the use of the compound for other applications. If the compound is added to cells in a tissue culture environment, such variables as pH, temperature and adjunct compounds can also be evaluated according to protocols standard in the art, to determine their influence on the efficacy of the compound under study to produce a detrimental effect in the cells. After an appropriate period of time following the contacting of the compound with the cells, the cells can be examined for such detrimental effects as cytopathology, cell death, etc. Those compounds demonstrating a detrimental effect on the cells of the present invention can then be tested in whole parasites for detrimental effects on the whole organism or administered to animals to test for the ability of the compound to treat or prevent parasite involvement with the animal.

The invention further provides a method of detecting the presence of a parasite in an animal, comprising contacting the parasite cells of the invention or fractions derived from the cells, which contain parasite antigens, with an antibody containing sample from the animal and detecting the presence of binding of the antibodies in the sample with the antigens in the cells or factions, the presence of binding indicating the presence of a parasite in the animal.

Well known detection methods, such as immunofluorescence assays (IFA), enzyme linked immunosorbent assays (ELISA) and Western blotting can be readily adapted to accomplish the detection of either parasite antigen or antibodies specifically reactive therewith. The specific reagents and protocols for use in the detection methods described herein and similar immunoassays can be selected from those available in the art based on standard criteria (Harlow and Lane, 1988).

One example of the method of detecting antibodies specifically reactive with parasite cells and cell fractions can be performed by contacting an antibody containing sample from the subject with an amount of the parasite cells or cell fractions of the present invention and detecting the reaction of the antibody with a parasite antigen. A specific embodiment of the antibody detecting method of the present invention can be an ELISA. Briefly, purified parasite cells or cell lysates are bound to a substrate (e.g., membrane, bead, plate); nonspecific proteins are blocked with a suitable blocking agent and then contacted with a sample from the subject for antibody capture by parasite antigen. A secondary antibody is then added, which binds to the antibody captured by the antigen. The secondary antibody can include an enzyme moiety which can produce a colored reaction product which can be detected by adding the appropriate enzyme substrate and observing and/or measuring the colored reaction product.

The invention also provides a method of detecting the presence of a parasite in an animal, comprising contacting antibodies of the invention with a sample from the animal potentially containing parasite antigen and detecting the presence of binding of the antibodies with a parasite antigen, the presence of binding indicating the presence of a parasite in the animal.

One example of the method of detecting parasite antigen is by contacting a fluid or tissue sample from the subject with an amount of a purified antibody of the present invention and detecting the reaction of the antibody with a parasite antigen. A specific embodiment of the antigen detecting method of the present invention can be an ELISA. Briefly, antibodies are bound to a substrate (e.g., membrane, bead, plate); nonspecific proteins are blocked with a suitable blocking agent and then contacted with a sample from the subject for parasite antigen capture by antibody. A second antibody is then added which binds to the antigen captured by the antibody. The second antibody can include an enzyme moiety which can produce a colored reaction product which can be detected by adding the appropriate enzyme substrate and observing and/or measuring the colored reaction product.

As contemplated herein, the antibody can include any ligand which binds a parasite antigen, for example, an intact antibody, a fragment of an antibody or any other reagent or compound that has reactivity with a parasite antigen. The subject sample of this method can comprise any tissue or body fluid which could contain a parasite antigen or a cell containing a parasite antigen, such as biopsy material, blood, plasma, serum, saliva and urine. Other possible examples of body fluids include sputum, mucus, semen gastric fluids, joint fluids, cavity fluids and the like.

Furthermore, the invention provides a method of culturing parasite cell populations in vitro comprising culturing a parasite in parasite culture medium (e.g., IPL-41 medium with antibiotics) under conditions which allow for decomposition and/or degradation of the cuticle layer of the parasite such that cellular buds are produced; disrupting the culture to cause the cellular buds to shear from the parasite cuticle layer; and culturing the parasite cellular buds in cell culture medium (e.g., a cocktail of IPL-41/SF900 media with antibiotics or only SF900 medium with antibiotics). This method can further comprise purifying the cellular buds on a Percol density gradient, rinsing the cells in PBS and inoculating the cells into cell culture medium. The cellular buds can be purified on a Percol density gradient shortly after cellular buds have started to form within and/or exterior to the parasite cuticle layer and the cellular buds can subsequently be removed from the gradient and placed into cell culture medium. The cellular buds can also be purified on a Percol density gradient after they have been transferred from the parasite medium to cell culture medium. Either or both of these density gradient purification steps can be carried out. A layer may also form in the Percol density gradient consisting of parasites from which cellular buds have only partially formed and parasites from which cellular buds have not yet formed. These parasites can be removed from the gradient and placed back into parasite culture medium and allowed to form cellular buds which can be harvested for culture. This step can be repeated until all of the parasites that are capable of forming cellular buds have done so. The parasite cell culturing method of this invention can also comprise transferring the cellular buds from the cell culture medium into fresh cell culture medium.

In this culture method, it is preferred that an average of at least two exterior cellular buds per parasite be produced prior to the disrupting step. It is also preferred that the disruption be mild, for example, at low speed centrifugation (200 to 400×g) in conical tubes, followed by serial aspiration by manual pipette. It is further preferred that the degradation be gradual, for example, the degradation or decomposition of the parasite cuticle layer can occur over two to three weeks as monitored by direct microscopic examination. However, some parasite species require shorter or longer periods of degradation and can be optimized by evaluation of the degradation process by direct microscopic examination.

The medium used for culturing parasites, particularly larvae, can be IPL-41 medium or other medium of similar composition to which antibiotics are added at concentrations of at least 50 to 100 mg/ml. For example, the parasite medium can be IPL-41 medium to which an aminoglycoside antibiotic (e.g., amikacin) has been added to a concentration of at least about 50 to 100 mg/ml and a β lactam and/or cephalosporin antibiotic (e.g., oxacillin) has been added to a concentration of at least about 50 to 100 mg/ml. Antifungal agents can also be added to the medium (e.g., fungizone at about 50 μg/ml). The parasite medium can also contain yeast extract as a non-serum protein source.

The cell culture medium can be IPL-41, SF900, a mixture of IPL-41/SF900 in any ratio, or other medium of similar composition to which antibiotics have been added to a concentration of at least 2.5 mg/ml. For example, the cell culture medium can be SF900 medium to which amikacin has been added to a concentration of about 2.5 mg/ml and oxacillin has been added to a concentration of about 5.0 mg/ml. Antifungal agents can also be added to the medium (e.g., fungizone at about 50 μg/ml). The cell culture medium can also contain yeast extract as a non-serum protein source.

The tissue culture flasks containing the cells of this invention can be filled with medium up to about 33 to 80% of total volumetric capacity. The flasks can be sealed and shaken (aerated) manually at the time of medium supplementation (i.e., at approximately one week intervals).

The method of the present invention can also comprise dissecting an organ from a larva at any stage, $L_1$–$L_5$, according to organ dissection protocols known in the art and placing the dissected organ into culture medium (e.g., IPL-41 medium with antibiotics) under conditions which allow for cellular buds to be produced; disrupting the culture to cause the cellular buds to shear from the dissected organ; and culturing the cellular buds in cell culture medium (e.g., IPL-41/SF900 media cocktail with antibiotics or SF900 medium with antibiotics). The same considerations, modifications and additional steps described herein as applicable to culturing a homogenous parasite cell population from parasites apply as well to dissected organs.

The viability of the cells of the homogenous population of the present invention can be determined with vital staining protocols well known in the art, such as, for example, the MTT (3-[4,5-dimethylthylthiazol-2-yl]-2,5-diphenyl tetrazolium bromide; Sigma) staining protocol (Coyne et al., 1993(a); Coyne et al., 1993(b)) described in the Examples herein. The cell types of the homogenous parasite cell populations can be identified by a variety of methods well known in the art. For example, the cells in culture can be examined microscopically to determine morphologically that all of the cells in the population are of the same type. Cell types can be further characterized by measuring or detecting the expression of cell specific markers, such as membrane antigens or enzymes. The expression of cell surface antigens can be detected by various immunocytochemical protocols well known in the art such as, for example, imumnofluorescence, flow cytometry (fluorescence activated cell sorting), immunostaining, immunoblotting, etc. Cell types can also be characterized by biochemical assays of cell specific enzymes employing enzyme specific substrates and by electron microscopy. Polymerase chain reaction (PCR) protocols can also be employed to characterize cell types by the presence of cell specific nucleic acids. Specific examples of how the parasite cell populations of the present invention can be characterized as to cell type can be found in the Examples provided herein.

The present invention further provides a population of parasite cells, not including mosquito cells, capable of prolonged culture in vitro, produced by the method of culturing a parasite in parasite culture medium (e.g., IPL-41 medium with antibiotics) under conditions which allow for decomposition and/or degradation of the parasite cuticle layer such that cellular buds are produced; disrupting the culture to cause the cellular buds to shear from the parasite cuticle layer; and culturing the parasite cellular buds in cell culture medium (e.g., a cocktail of IPL-41/SF900 media cocktail with antibiotics or only SF900 medium with antibiotics). The population of parasite cells produced by this method can be either a homogenous population of parasite cells wherein the parasite cells are substantially of one cell type as defined herein or a heterogenous population of parasite cells wherein the parasite cells are not substantially of one cell type. The population of cells produced by this method can be of any type of parasite cells and preferably are parasite intestinal cells. These cells can be lysed, fractionated and/or provided in a pharmaceutically acceptable carrier under all of the same conditions as described herein. In addition, antigens from these cells can be isolated and purified as described herein and used as immunogens in vaccine preparations and for the production of antibodies and anti-idiotype antibodies as described herein. The amino acid and nucleic acid sequences of the proteins of these cells can be determined as described herein and the genes for the proteins of these cells can be cloned and expressed in appropriate expression systems.

The parasite from which the population of cells is obtained by the method described herein can be from any parasite as described above and is preferably a nematode and most preferably is a nematode selected from the group consisting of species of Cooperia, Oesophagostomum, Ostertagia, Haemonchus, Dirofilaria and Dictyocaulus.

Finally, in a particular embodiment, the present invention provides a population of differentiated nematode cells capable of prolonged culture in vitro. As used herein, "differentiated" means that the cells have originated from an organ/tissue system from a developed parasite (e.g., $L_1$–$L_5$ stage larvae and/or adult parasites) as determined by the expression of antigens and/or enzymatic activities known to be expressed only by larval and adult parasites. The expression of such antigens and/or enzymatic activities can be detected according to the protocols provided in the Examples herein.

The population of nematode cells can be either a homogenous population of nematode cells wherein the nematode cells are substantially of one cell type as defined herein or a heterogenous population of nematode cells wherein the nematode cells are not substantially of one cell type. The population of nematode cells produced by this method can be of any type of nematode cells and preferably are nematode intestinal cells. These cells can be lysed, fractionated and/or provided in a pharmaceutically acceptable carrier under all of the same conditions as described herein. In addition, antigens from these cells can be isolated and purified as described herein and used as immunogens in vaccine preparations and for the production of antibodies and anti-idiotype antibodies as described herein. In addition, the amino acid and nucleic acid sequences of the proteins of these cells can be determined as described herein and the genes for the proteins of these cells can be cloned and expressed in appropriate expression systems.

The nematode from which the population of nematode cells is obtained can be any nematode and most preferably is a nematode selected from the group consisting of species of Cooperia, Oesophagostomum, Ostertagia, Haemonchus, Dirofilaria and Dictyocaulus.

The present invention is more particularly described in the following examples which are intended as illustrative only since numerous modifications and variations therein will be apparent to those skilled in the art.

EXAMPLES

Preparation, Purification and Propagation of Parasite Cell Populations

Parasitic $L_3$ stage larvae from species of Cooperia, Haemonchus (e.g., *Haemonchus contortus*), Oesophagostomum, Ostertagia (e.g. *Ostertagia ostertagi*), Dictyocaulus (e.g., *Dictyocaulus viviparous*) and Dirofilaria (e.g., *Dirofilaria immitus*) nematodes were utilized as a source for preparing homogenous parasite cell populations in vitro. $L_3$ stage larvae were selected on the basis that, at this developmental stage, cells of the parasite's gastrointestinal tract predominate over other cell types because the organism's other organ systems are still very immature. Thus, the likelihood that cells obtained from the cellular buds of L3-stage larvae are intestinal cells is substantially increased. However, any stage of parasite larvae (e.g., $L_1$, $L_2$, $L_4$, $L_5$) of parasite larvae may be used as starting material in the present invention.

Initial Larval Preparations: Bacterial Decontamination and Removal of Fecal Plant Debris Viable larval populations ingest bacteria flora and plant debris as a source of nutrients from the lumen of the host's intestinal tract. For this reason, viable larval preparations were suspended in physiological saline supplemented with antibiotic and antifungal formulations (ampicillin, oxacillin, fungizone) and incubated at 4° C. for 24 to 48 hours to decontaminate preparations prior to tissue culture procedures. Antibiotic treated larvae were rinsed in sterile phosphate buffered saline (PBS) (pH 7.4), and separated from fecal debris on Percol density gradients (S.G. 1.025, 1.050, 1.075, 1.100). Larval populations which concentrated in stratified bands were harvested by pipette and their identity verified by light microscopy. Harvested larvae were then suspended in PBS and centrifuged at low speed (200×g). The resulting supernatant containing residual Percol density gradient medium was removed by pipette and discarded. Rinsing of the larvae to remove all of the Percol density gradient medium is necessary as it adversely affects formulations of tissue culture medium. Separation procedures by Percol density gradient are repeated as necessary to obtain an increasingly pure larval rich preparation devoid of contaminating fecal plant material. Frequently, there is a minimal amount of debris which cannot be separated from larvae by Percol density gradient purification alone. Larval preparations can be further purified by differential centrifugation utilizing low-speed (200–300×g) centrifugation, and/or gravity sedimentation.

Alternative procedures which are effective for the separation and harvest of viable larval populations from fecal plant debris can include the application of a fine wire mesh partition or multiple layers of cloth. In this procedure, larvae which have actively migrated to the other side of a fine wire mesh or cloth layers are collected for culture (Baerman technique; Ivens et al., 1978).

Propagation of Parasite Cell Populations in a Tissue Culture (In Vitro) Environment Larvae which have been decontaminated of bacterial flora and fecal plant material, in addition to removal of residual Percol density gradient medium, are inoculated into tissue culture flasks containing serum-free growth medium such as Grace's, IPL-41 (Cooperia, Haemonchus, Oesophagostomum), or SF-900 (Ostertagia) tissue culture medium supplemented with amikacin (50–100 mg/ml), oxacillin (50–100 mg/ml) and fungizone (50 µg/ml). Following antibiotic and antifungal supplementation, larval medium has a final pH of approximately 4.5 in conditions of 5.9% $CO_2$ and humidified air. The tissue culture flasks are periodically aerated by gentle agitation. The larval cultures are incubated at 37° C. for a period of between 14 to 21 days, during which time the cuticle layer of the larvae is gradually degraded and cells can be observed to protrude through defects in the cuticle layer of individual larvae (cellular "budding"). The antibiotic concentration and pH level of the medium appear to directly affect the extent of this process and the rate at which this process progresses.

Optimal cellular "budding" has been demonstrated with IPL-41 tissue culture medium, in contrast to other formulations evaluated. The relatively low pH of this modified tissue culture medium may simulate the abomasal environment to which many of the larval populations have adapted. Bacterial flora may potentially improve the propagation of parasite cell populations (e.g., intestinal cells) in a tissue culture environment, based upon the ingestion of such organisms by intact parasites as a source of nutrients. If tissue culture flasks become excessively "contaminated" with bacterial growth, additional antibiotic reagents can be added to culture flasks. Growth medium is then screened for contaminating bacterial growth by inoculation of the medium onto MacConkey's, Mueller-Hinton and blood agar plates.

Flasks are inspected on a regular basis under an inverted microscope to detect cellular "budding" through defects in the cuticle layer of the larvae. When "budding" has been achieved, the larval culture is subjected to mild disruption by serial pipetting in conjunction with low-speed centrifugation. This procedure appears to gently "shear" off cellular "buds" and lightly collapses the cuticle layer. As a result, parasite cells are "squeezed" or extruded out from within the lumen of the cylindrically shaped cuticle layer. This approach allows the gentle harvesting of parasite cells which have been allowed to proliferate in situ without excessive disruption. Further separation of viable cells from the cuticle and other non-viable debris can be achieved by layering the larval culture material on a Percol density gradient, centrifuging the gradient to separate the cellular buds from the other materials, separating the cellular buds from the gradient, rinsing the cellular buds in PBS and re-inoculating the cellular buds into tissue culture flasks containing cell culture medium (e.g. IL-41/SF900 media cocktail or SF900 medium only) supplemented with amikacin (2.5 mg/ml), oxacillin (5.0 mg/ml) and fungizone (amphotericin B) (50 µg/ml).

Parasite cells appear to optimally propagate in vitro when fresh cell culture medium is periodically infused into the tissue culture flasks at regular intervals. Addition of medium is therefore performed on an as-needed basis, usually at about one week intervals, depending on the existing level of proliferation, as assessed by direct visual observation and examination under an inverted microscope. For example, cellular buds are initially transferred to 75 cm$^2$ tissue culture flasks and approximately 15 ml of cell culture medium is added. At about one week intervals, a small volume of fresh medium is added and the flask is aerated by agitation. This is repeated until the medium volume reaches approximately 50 ml, at which time the cells and medium are transferred to a 250 cm$^2$ tissue culture flask and fresh medium is added for an initial volume of approximately 60 ml. Medium is added at approximately one week intervals with shaking, until the medium volume reaches approximately 225 mls. The cells and medium are then transferred to a 500 cm$^2$ tissue culture flask and fresh medium is added at about one week intervals with shaking until the medium volume reaches approximately 450 ml. At this time, the cells are split into multiple flasks as described herein.

Once the capacity of a tissue culture flask has been exceeded as determined by medium volume and microscopic observation of a substantial amount of cellular sediment in the bottom of the tissue culture flask, the cells are "scraped" from the flask by sterile technique and are either transferred (passaged) to a larger tissue culture flask or "split" 50/50 or 33/33/33 between two or three flasks. In either "splitting" situation, additional fresh cell culture medium is added to each tissue culture flask. It has been observed that, if all of the medium of the tissue culture flask is replaced with fresh cell culture medium when the parasite cells are being passaged (which is what is typically done in mammalian tissue culture), the parasite cells demonstrate a lag in or termination of proliferation and antigen expression. Therefore, when the cells are passaged, fresh cell culture medium is typically added to the tissue culture flask in a ratio of between 33 and 50% "spent" cell culture medium and 67 and 50% fresh cell culture medium, although any ratio of spent to fresh cell culture medium can be used so long as the percentage of spent medium is at least 10–15%.

Stimulation of Delayed Proliferation Rate

Parasite cell populations will occasionally display patterns of delayed growth and proliferation rates. In such instances, several procedures can be applied to stimulate cell division and propagation. Examples of procedures which have been effective include (a) low-speed centrifugation and resuspension of the pellet in the same "spent" growth medium; (b) cryopreservation in liquid nitrogen for a brief period of time (e.g., at least 48 hours) and then recultivation in fresh cell culture medium; (c) sterile "scraping" of cells from the surfaces of the tissue culture flasks; (d) avoidance of exposure of the tissue culture flasks to atmospheric air for several days; (e) positioning of tissue culture flasks on a diagonal slant; and (f) inoculation of loose cellular pellets into "spent" medium following low-speed (200–300×g) centrifugation.

Cell Lysis, Fractionation and Antigen Sample Preparation

Parasite cells were centrifuged at 200×g to form a cell pellet, the medium was discarded and the cell pellet was resuspended in Triton X-100 (1–5%) supplemented with EDTA (2–5 mM), and aprotinin (3 mg/ml) at 0° to 4° C. (ice bath). The cells were incubated at 25° C. for one hour with periodic gentle agitation and then centrifuged at 500×g. The resulting supernatant extract was harvested.

Excessive processing of parasite cellular pellets can disrupt their integrity and/or alter the harvesting of important antigenic and/or enzymatic fractions. Pelleting of parasite cell populations ideally should be by single low-speed centrifugation (e.g. 200×g) for a relatively brief period of time at 4° C. The centrifugation procedure to harvest parasite cell populations should only be performed once. If a second centrifugation procedure is necessary to harvest parasite cells into a single collective pellet, then the resulting "second" supernatant should be harvested for analysis and not discarded. The basis for this precaution is founded upon the observation that membrane-associated antigens (e.g., aminopeptidase-M) are apparently easily "leached" off of the external surface of parasite cells.

Only "spent" or fresh cell culture medium should be employed during centrifugation procedures to suspend and harvest parasite cells in vitro. Application of buffer systems such as PBS and Tris-HCl, which are traditionally considered physiologically gentle to mammalian cell populations, appear to excessively disrupt and substantially reduce the cellular mass harvested.

Verification of Cellular Viability and Estimation of In Vitro Proliferation Rate Parasite cells were transferred in aliquots (300 µl) into individual compartments of a 48-well microtiter plate. A 60 µl aliquot of MTT (Sigma) vitality staining reagent was added to each well and the plates were incubated in a humidified incubator at 37° C. for 12 hours. The microtiter plates where then centrifuged, the resulting supernatant removed by pipette and the parasite cells were destained with acid isopropyl alcohol for 20 minutes at 25° C. The resulting supernatant was transferred by pipette to a 96-well microtiter plate and absorbance of each well was read at 450 nm utilizing a computer-integrated mnicrotiter plate reader. Assays were repeated at various times to estimate the approximate proliferation rate (doubling time) of parasite cells propagated in a tissue culture environment.

The MTT reagent is reduced to navy-blue formazone crystals within the cytosol of viable cells, which is subsequently solubilized with acid isopropyl alcohol prior to measurement of spectrophotometric absorbance at 450 nm. Mammalian cells and bacteria reduce MTT reagent to formazone crystals in approximately 3–4 hours and 15 minutes, respectively. Parasite cells reduced MTT reagent to intracellular formazone crystals over a period of 8 to 12 hours.

Verification of Homogeneity of In Vitro Cell Populations

Populations of parasite cells were examined under an inverted microscope and evaluated morphologically to determine homogeneity of the cell population. The cells were examined for uniformity in shape and size, the appearance of fine granules within the cells and the presence of variable sized aggregates or clumps of cells in the culture flask. The parasite cells of the present invention were observed to all be of a uniform size and shape and to all contain fine granules, of similar appearance in all of the cells observed. Thus, on the basis of these observations of the morphological features of the cells of this invention, it appeared that all of the cells were of a single cell type, demonstrating that the parasite cells in culture consisted of a homogenous population of cells.

Verification of Viability and Estimation of Proliferation Rate

The proliferation rate of Ostertagia and Haemonchus cells propagated in vitro as described herein was determined with the application of MTT vitality staining reagent to be as follows:

Ostertagia:
  Flask 1: 8.9 fold increase/6 days
  Flask 2: 3.5 fold increase/14 days
Haemonchus:
  Flask 1: 1.5 fold increase/6 days
  Flask 2: 1.49 fold increase
  Flask 3: 1.90 fold increase These data demonstrate that the parasite cells of this invention were viable and proliferating under the culture conditions described herein.

Analysis of Surface Membrane Antigens by SDS-PAGE

Samples of "spent" growth medium and Triton X-100 (1–5%) detergent solubilized extracts of parasite cells were analyzed by non-denaturing SDS-PAGE (10% acrylamide, 20 constant voltage, 40° C.) according to standard techniques (Laemmli, 1970). The gels were silver stained according to standard methods to identify membrane associated antigens produced by the parasite cells of the homogenous cell population.

SDS-PAGE Analysis

Estimates of the observed molecular weights of membrane-associated antigens (in kDa) expressed by parasite cell populations propagated in vitro are shown below.

| MW (kDA) | 12 | 14 | 18 | 20 | 29 | 32 | 40 | 50 | 60 | 70 | 80 |
|---|---|---|---|---|---|---|---|---|---|---|---|
| Parasite | | | | | | | | | | | |
| Ostertagia | M | H | L | L | L | H | M | H | M | — | — |
| Haemonchus | M | M | M | M | — | H | M | H | M | M | H |
| Oesophagostomum | H | — | M | — | — | — | — | H | — | L | — |
| Cooperia | M | M | L | L | H | L | L | L | H | M | H |

H = high-level of expression relative to other protein fractions identified within the same lane (sample).
M = moderate-level of expression relative to other protein fractions identified within the same lane (sample).
L = low-1evel of expression relative to other protein fractions identified within the same lane (sample)

Additional membrane-associated antigens expressed by parasite cells of the present invention include the following:
  Haemonchus, Cooperia 120 kDa
  Haemonchus, Cooperia, Oesophagostomum 180 kDa These experimental findings serve to: (a) partially characterize the identity of cell lines presently being propagated in vitro; (b) demonstrate a relatively minimal loss of membrane-associated antigen expression in parasite cell populations propagated for extended periods in vitro; and (c) identify membrane-associated proteins/glycoproteins which may be "shared" antigens expressed by each of the four genera of bovine parasites described herein. Such "shared" membrane-associated antigens can provide a means for inducing "cross-reactive" protective immunity to these parasites in challenged hosts.

Western Blot Analysis of Microfilarial Membrane-Associated Antigens

Membrane-associated antigens were harvested from microfilaria cell populations by extraction with detergent (e.g., Triton X-100, Thesit). Proteins in the fraction were separated according to molecular weight with SDS-PAGE. Proteins were transferred to nitrocellulose membranes according to standard blotting protocols (Harlow and Lane, 1988; BioRad catalog and manual). A monoclonal antibody (Catalog # DFI 023-40470; Capricorn Products, Inc., Scarborough, Me.), directed against an antigen expressed by adult canine heartworms (*Dirofilaria immitus*) was added to the nitrocellulose membranes. An anti-murine secondary antibody conjugated to horseradish peroxidase (HRPO) (Pierce Chemicals) was then added to the membranes and $H_2O_2$ was added to the membrane for development of a detectable color reaction.

SDS-PAGE Western Blot Analysis

Monoclonal antibody directed against antigen expressed by adult canine heartworms (*Dirofilaria immitus*) displayed binding avidity for fractions containing membrane associated antigens solubilized from microfilaria cell populations. These experimental findings indicate that the cells cultured from microfilaria larvae have been successfully propagated in a tissue culture environment and that the cultured cells are microfilarial cells which continue to express the antigen bound by the monoclonal antibody.

Detection of Proteolytic Enzyme Fractions by Gelatin SDS-PAGE

Samples of "spent" growth medium and Triton X-100 detergent extracts of parasite cells were analyzed for proteolytic enzyme activity by non-denaturing (non-reducing) gelatin SDS-PAGE (0.1% gelatin, 10% acrylamide, 20 constant voltage, 40° C.) (McKerrow et al., 1990; Gambel et al., 1996). Gels were rinsed (20 minutes×3) in Triton X-100 (2.5%) and incubated 24–48 hours at 37° C. in Tris-HCl (0.1 M, pH 7.0) supplemented with $CaCl_2$ (1 mM). Gelatin SDS-PAGE gels were stained with Coomassie Brilliant Blue 450 (0.1%) (Sigma) for three hours at 25° C., followed by destaining in methanol-acetic acid in water (35:10 v/v).

Proteolytic enzymes were detected as clear zones against the gelatin SDS-PAGE background positively stained with Coomassie Brilliant Blue 450, signifying enzymatic degradation of the gelatin matrix. In *Ostertagia ostertagi* cells, proteolytic enzyme activity was detected in protein fractions having the approximate molecular weights of >200 kDa, 116–150 kDa, 63–75 kDa and 45 kDa. Proteolytic fractions located at 116–150 kDa and at 63–75 kDa were very subtle in appearance. In *Haemonchus contortus* cells, proteolytic enzyme activity was detected in a protein fraction having the approximate molecular weight of 30 kDa. These results match the gelatin SDS-PAGE profiles of known whole parasite larvae, demonstrating that the Ostertagia and Haemonchus cells of the present invention are larval cells and that the cells in culture are producing proteolytic enzymes.

Assays for Aminopeptidase-M Proteolytic Activity

Aminopeptidase-M is an enzyme produced in parasite intestinal cells (McMichael-Phillips et al., 1995), therefore, an assay for aminopeptidase M activity was conducted to further characterize the homogenous parasite cell population as to cell type. Precautions were exercised in the processing of parasite cell populations for the assay of aminopeptidase-M activity because this enzyme appeared to "leach" off of the external membrane during processing.

Experimental samples (50 $\mu$l) of spent medium, rinsed, whole cells and mechanically disrupted whole cells or Triton X-100 extracts of cell pellets were combined with MOPS buffer (50 mM, pH 7.0, 100 $\mu$l) and incubated at 25° C. for 15 minutes in a 96-well microtiter plate to allow the enzyme to equilibrate in this buffer. At the end of the incubation period, the enzyme specific substrate reagents, leucine-paranitroanalide (pNA)and methionine-pNA (2 mM, 100 $\mu$l) were added into individual wells. Plates were incubated for variable times (0 to 48 hours) in a humidified incubator at 37° C. and the presence of aminopeptidase-M was determined by measurement of the proteolytic liberation of pNA as detected by spectrophotometric absorbance at 405 nm. In addition, spent medium and Triton X-100 samples were fractionated by molecular weight in a microfiltration device (Amicon, Inc., Beverly, Mass.) and prepared as described above. Negative controls included the application of the metal (zinc) chelating reagent, 1,10 phenanthroline (10 mM, 4 μl), to wells containing experimental sample, buffer and enzyme substrate, because aminopeptidase enzymes are classified as zinc metalloproteases. Positive controls included porcine aminopeptidase-M (Sigma, St Louis, Mo.), buffer and enzyme substrate.

Aminopeptidase-M Expression

Results from the spectrophotometric assay for aminopeptidase M demonstrated that this enzymatic activity was present in the whole cell preparations, "spent" medium samples and detergent solubilized membrane associated antigen fractions of the parasite cell populations of *Ostertagi ostertagi* and *Haemonchus contortus*, Oesophagostomum, *Dirofilaria immitus* and Cooperia of the present invention. Results from experiments in which the samples were fractionated by molecular weight prior to assay demonstrated that the aminopeptidase activity was present in fractions of approximately 45–50 kDa and >100 kDa molecular weight. In the presence of the metal chelating agent, 1,10 phenanthroline, no aminopeptidase-M activity was detected in any experimental samples.

These data demonstrate that the Ostertagia and Haemonchus cells of the present invention are intestinal cells on the basis that these cells express proteins having aminopeptidase-M activity and the proteins expressing this activity are of molecular weights similar to proteins extracted from parasite intestinal cells which are known to express aminopeptidase-M activity (McMichael-Phillips et al., 1995).

Assays for Phosphorylase Activity

In addition to aminopeptidase-M, assays for phosphorylase (phosphorylhydrolase), another enzyme known to be produced in parasite intestinal cells (Gambel et al., 1980; Knowles and Oakes, 1979; Gambel & Mansfield, 1996; Gambel et al., 1996; Barrett, 1981) were carried out to further characterize the cells of the homogenous cell populations as parasite intestinal cells. To detect phosphorylase activity in the parasite cells of this invention, the protocol described above for detection of aminopeptidase-M activity was carried out with the exception that the phosphorylase-specific substrate, paranitrophenylphosphate, was substituted for the aminopeptidase-M substrate. Experimental samples possessing phosphorylase activity were identified by the development of a yellow color representing the enzymatic release of the chromogenic moiety from the substrate as detected by measurement of absorbance at 405 nm. Negative controls contained tartaric acid (1 mM) as a phosphorylase inhibitor.

Phosphorylase Expression

Phosphorylase activity was detected in experimental samples from *Ostertagia ostertagi, Dictyocaulus vivaparus, Haemonchus contortus* Cooperia, Oesophagostomum and *Dirofilaria immitus* cells in culture. Because this enzyme is known to be expressed by parasite intestinal cells, these data provide further support that the parasite cells of the present invention are intestinal cells.

Assays for Other Enzymes Markers

Assays for enzymes known to be produced in parasite cells of types other than intestinal cells were also carried out according to the protocol described above to further characterize the cultured parasite cells of the present invention. For example, phospholipase-C, chymotrypsin, cathepsin C, dipeptidylpeptidase and N-acetylglycosamidase have all been detected in excretory-secretory products in fourth stage larvae (Gamble and Mansfield, 1996) and have not been detected in parasite intestinal cells. The other enzymes for which screening was carried out and the specific substrates which were used were as follows:

| Enzyme marker: | Enzyme specific substrate: |
|---|---|
| phospholipase-C | para-nitrophenylphosphorylcholine |
| chymotrypsin | succinyl-phenylalanine paranitroanilide |
| cathepsin C | glycine-phenylalanine paranitroanalide |
| dipeptidylpeptidase IV | glycine-proline paranitroanalide |
| N-acetyl-β-D-glucosamidase | paranitrophenyl-N-acetyl-β-D-glucosamide |

Detection of Expression of Other Parasite Cell Enzyme Markers

Assays of the Ostertagia and Haemonchus cells of the present invention for expression of phospholipase-C, chymotrypsin, cathepsin C, dipeptidylpeptidase IV and N-acetylglycosamidase, with the respective enzyme-specific substrates listed above, all yielded negative results. These results provide further support that the Ostertagia and Haemonchus parasite cells of the present invention are intestinal cells on the basis that none of the cells demonstrated any phospholipase-C, chymotrypsin, cathepsin C, dipeptidylpeptidase IV or N-acetylglycosamidase activity, which is consistent with what would be expected in intestinal cells and that the aminopeptidase-M and phosphorylase activity detected in these cells is not associated with excretory-secretory products. These data also show that the cell populations of the present invention do not contain cells of the types which express these enzymes, further demonstrating that the cell populations of the present invention are homogenous.

Ligand Binding Analysis with Concanavalin A Lectin

Experimental samples of "spent" tissue culture medium and Triton X-100 detergent solubilized extracts were applied to nitrocellulose membranes utilizing a 96-well Dot Blot apparatus in combination with negative pressure (BioRad). Non-specific binding was minimized by incubating nitrocellulose membranes in bovine serum albumin (BSA) or skim-milk as blocking buffer (Tris 100 mM, pH 7.4), for two hours at 25° C. Nitrocellulose membranes wee rinsed (3×20 minutes) in Tris-HCl (50 mM, pH 7.0). Biotinylated concanavalin-A (Con-A; 10 μg/ml) (EY Labs) was added to the nitrocellulose membranes for 90 minutes at 25° C. Residual biotinylated Con-A was removed by rinsing (3×20 minutes) in Tris-HCl (50 mM, pH 7.0). Streptavidin-horseradish peroxidase (streptavidin-HRPO; 2 μ/ml of a 0.5 mg/ml stock) (Pierce Chemical Co.) in Tris-HCl (50 nM, pH 7.0) was added to the nitrocellulose membranes for 90 minutes at 25° C. Membranes were again rinsed (3×20 minutes) in Tris-HCl and final development of a detectable reaction was achieved by addition of $H_2O_2$ (2 μl/ml of a 30% solution) which functions as a catalyst for the enzymatic activity of horseradish peroxidase.

Lectin (Biotinylated Con-A) Dot Blot Analysis

Binding of Con-A to experimental samples from spent medium and Triton X-100 fractions was detected by the development of a visible reaction product on the nitrocellulose membranes. The results of these experiments demonstrated that proteins contained in both "spent" growth medium and Triton X-100 detergent extracts of parasite cells propagated in vitro displayed positive binding avidity for biotinylated Con-A reagent.

Ligand Affinity Gel Extracts of "Spent" Growth Medium and Membrane-Associated Antigens Experimental samples of "spent" growth medium and membrane-associated antigens were applied to sepharose conjugated Con-A in buffer A (pH 5.2) consisting of sodium acetate (5 mM), manganese chloride (1 mM), calcium chloride (1 mM), sodium chloride (0.1 mM) and sodium azide (0.02%). Following extensive rinsing of the sepharose Con-A gel with buffer A, bound protein fractions were displaced from the gel utilizing buffer B (pH 5.2), consisting of methyl-alpha-D-glucopyranoside (0.5 M) and methyl-mannoside (0.2 M) and subsequently harvested in the resulting supernatant. Portions of these samples were then analyzed by SDS-PAGE under reducing conditions to determine the approximate molecular weights of the Con-A binding proteins in the parasite cells.

In addition, protein fractions possessing Con-A binding avidity were further assayed for aminopeptidase-M activity according to the protocol described above.

SDS-PAGE of Con-A Binding Proteins

Proteins from *Ostertagia ostertagi* and *Haemonchus contortus* cells having Con-A binding activity had approximate molecular weights of >200 kDa, 100–116 kDa, 50–55 kDa, 40–45 kDa and 29–33 kD. Furthermore, these Con-A binding fractions were shown to possess aminopeptidase-M activity. The significance of these data is that analogous proteins of similar molecular weights harvested from parasite intestinal cells possess both aminopeptidase-M activity and Con-A binding avidity (McMichael-Phillips et al., 1995).

Although the present process has been described with reference to specific details of certain embodiments thereof, it is not intended that such details should be regarded as limitations upon the scope of the invention except as and to the extent that they are included in the accompanying claims.

Throughout this application, various publications are referenced. The disclosures of these publications in their entireties are hereby incorporated by reference into this application in order to more fully describe the state of the art to which this invention pertains.

REFERENCES

1. Agbede R I S, Kemp D H. Immunization of cattle against *Boophilus microplus* using extracts derived from adult female ticks; Histopathology of ticks feeding on vaccinated cattle. *International Journal of Parasitology* 1986;16:35–41.
2. Alger N E, Cabrera E J. An increase in death rate of *Anopheles stephensi* fed on rabbits immunized with mosquito antigen. *Journal of Economic Entomology* 1972;65:165–168.
3. Allen J R, Humphreys S J. Immunization of guinea pigs and cattle against ticks. *Nature* (London) 1979;280:491–493.
4. Baker N F R A, Fisk R B, Bushnell R B, Oliver M N. Seasonal occurrences of infective nematode larvae on irrigated pasture grazed by cattle in California. *Am J Vet Res* 1981;42:1188–1191.
5. Bautista-Garfias C R, Flores-Hernadez O, Quiroz-Romero H. Non-specific resistance to sheep against *Haemonchus contortus* with Freund's complete adjuvant. *Parasite Immunology* 1991;13:565–569.
6. Boisvenue R J, Stiff M I, Tonkinson L V, Cox G N. Protective studies in sheep immunized with cuticular collagen proteins and peptides of *Haemonchus contortus*. *Parasite Immunology* 1991;13:227–240.
7. Borgsteede F H M. Further studies with a strain of *Ostertagia ostertagia* resistant to morantel tartrate. *International Journal of Parasitology* 1988;18:499–502.
8. Borgsteede F H M. Further studies with a strain of *Ostertagia ostertagia* resistant to morantel tartrate. *International Journal of Parasitology* 1991;21:867–870.
9. Bremner K C. The parasitic life-cycle of *Haemonchus placei* (Place)Ransom (Nematoda:Trichostrongylidae). *Australian Journal of Zoology* 1957;4:146–151.
10. Brunsdon R V. Principles of helminth control. *Veterinary Parasitology* 1980;6:185–215.
11. Canals A, Gasbarre L C. *Ostertagia ostertagia:* isolation and partial characterization of somatic and metabolic antigens. *International Journal for Parasitology* 1990;20:1047–1054.
12. Craig T M. Seasonal transmission of bovine gastrointestinal nematodes in the Texas gulf coast. *J Am Vet Med Assoc* 1979;174:844–847.
13. Craig T M. Anthelmintic Resistance. *Veterinary Parasitology* 1993;46:121–131.
14. Cuquerella M, Gomez-Munoz M T, Alunda J M. Serum IgG response of Manchego lambs to infections with *Haemonchus contortus* and preliminary characterization of adult antigens. *Veterinary Parasitology* 1991;38:131–143.
15. Drudge J H, Leland S E, Wyant Z N. Strain variation in the response of sheep nematodes to the action of phenothiazine I. Studies on pure infections of *Haemonchus controtus*. *Am J Vet Res* 1957;18:317–325.
16. Durie P H. Parasitic gastro-enteritis of cattle: the distribution and survival of infective strongyle larvae on pasture. *Australian Journal of Agriculture* 1961;12:1200–1211.
17. Durie P H. Parasitic gastro-enteritis of cattle: seasonal fluctuations in populations of strongyle larvae on calf pasture and their significance in infection of the grazing animal. *Australian Journal of Agricultural Research* 1962;13:767–777.
18. Eagleson J S, Bowie J Y. Oxfendazole resistance in *Trichostrongylus axei* in cattle in Australia. *Veterinary Record* 1986;119:604–612.
19. Fitzsimmons W M, Harness E. Attempts by blood transfusion, to replace blood loss due to *Haemonchus placei* infection. *Veterinary Record* 1969;84:49–50.
20. Gasbarre L C. Genetic control of immunity to gastrointestinal nematodes of cattle. *Veterinary Parasitology* 1990;37:257–272.
21. Gasbarre L C, Leighton E A, Davies C J. Influence of host genetics upon antibody responses against gastrointestinal nematodes infections in cattle. *Veterinary Parasitology* 1993;46:81–91.
22. Geerts S, Brandt J, Kumar V, Biesemons L. Suspected resistance of *Ostertagia ostertagia* in cattle to levamisole. *Veterinary Parasitology* 1987;23:77–82.
23. Gennari S M, Vieira Bressan C R, Rogero J R, MacLean J M, Duncan J L. Pathophysiology of *Haemonchus placei* infections in calves. *Veterinary Parasitology* 1991;38:163–172.
24. Gibbs H C, Herd R P. Nematodiasis in cattle: Importance, species involved, immunity and resistance. *Veterinary Clinics of North America: Food Animal Practice* 1986;2:211–224.
25. Harness E, Fitzsimmons W M. Experimental *Haemonchus placei* infection in cattle: Blood picture at three levels of infection. *Journal of Comparative Pathology* 1970;80:173–179.
26. Harness E, Sellwood S A, Young E R. Experimental *Haemonchus placei* infection in calves: Influence of anaemia and numbers of larvae on worm development. *Journal of Comparative Pathology* 1971;81:129–136.
27. Harness E, Smith K, Bland P. Structural changes in the bovine nematode *Haemonchus placei* that may be associated with host immune response. *Parasitology* 1973;66:199–205.
28. Hawkins J A. Economic benefits of parasite control in cattle. *Veterinary Parasitology* 1993;46:159–173.

29. Heath A W, Arfsten A, Yamanaka M, Dryden M W. Vaccination against the cat flea *Ctenocephalides felis*. *Parasite Immunology* 1994;16:187–191.
30. Jackson R A, Townsend K G, Pyke C, Lance D M. Isolation of oxfendazole resistant *Cooperia oncophora* in cattle. *New Zealand Veterinary Journal* 1987;35:187–189.
31. Jasmer D P, McGuire T C. Protective immunity to a blood-feeding nematode (*Haemonchus contortus*) induced by parasite gut antigens. *Infection and Immunity* 1991;59:4412–4417.
32. Jasmer D P, Perryman L E. A phylogenically conserved gut surface antigen(s) of *Haemonchus contortus* and its' efficacy in inducing protective immunity. *Proc 37th Annual AAVP Meeting,* Aug. 2–4, 1992.
33. Johnston L A Y, Kemp D H, Pearson R D. Immunization of cattle against *Boophilus microplus* using extracts derived from adult female ticks: Effects of induced immunity on tick populations. *International Journal of Parasitology* 1986;16:27–34.
34. Kelly J D, Hall C A. Resistance of animal helminths to anthelmintics. *Advances in Pharmacology and Chemotherapy* 1979;16:89–128.
35. Kemp D H, Agbede R I S, Johnston L A Y. Immunization of cattle against *Boophilus microplus* using extracts derived from adult female ticks: Feeding and survival of the parasite on vaccinated cattle. *International Journal for Parasitology* 1986;16:115–120.
36. Kimaro E E, Opdebeeck J P. Tick infestations on cattle vaccinated with extracts from the eggs and the gut of *Boophilus microplus*. *Veterinary Parasitology* 1994;52:61–70.
37. Krecek R C, Groeneveld H T, van Wyk J A. Effects of time of day, season and stratum on *Haemonchus contortus* and *Haemonchus placei* third-stage larvae on irrigated pasture. *Veterinary Parasitology* 1991;40:87–98.
38. Lanusse C E, Prichard R K. Relationship between pharmacological properties and clinical efficacy of ruminant anthelmintics. *Veterinary Parasitology* 1993;49:123–158.
39. Lee R P, Opdelbeeck J P. Isolation of protective antigens from the gut of *Boophilus microplus* using monoclonal antibodies. *Immunology* 1991;72:121–126.
40. Leighton E A, Murrel K D, Gasbarre L C. Evidence of genetic control of nematode egg-shedding rates in calves. *Journal of Parasitology* 1989;75:498–504.
41. Levine N D. Weather, climate and bionomics of ruminant nematode larvae. *Advances in Veterinary Science* 1963;8:215–261.
42. Levine N D. *Nematode parasites of domestic animals and man*. Burgess Publishing Company 1980; 2nd ed.:162–163.
43. Lyons E T, Tolliver S C, Drudge J K, Hemken R W. Efficacy of levamisole against abomasal nematodes and lungworms in dairy calves: Preliminary tests indicating reduced activity for *Ostertagia ostertagia*. *Am J Vet Res* 1981;42:1228–1230.
44. Maizels R M, Kennedy M W, Meghi M. Shared carbohydrate epitopes on distinct surface and secreted antigens of the parasitic nematode, *Toxocara canis*. *Journal of Immunology* 1987;139:207–214.
45. Mayhew R L. Studies on bovine gastrointestinal parasites V. Immunity to the stomach worm, with a note on the prepatent period. *Am J Hygiene* 1941;33:103–111.
46. McGowan M J, Barker R W. Success of tick feeding on calves immunized with *Amblyomma americanum* (Acari:Ixodidae) extract. *J Med Entomol* 1981;18:328–332.
47. Miller J E. Observations on nematode parasitism in cow-calf production systems in southcentral-southwestern U.S.A. *Veterinary Parasitology* 1993;46:289–295.
48. Munn E A. Development of a vaccine against *Haemonchus contortus*. Parasitology Today 1993;9:338–339.
49. Munn E A. Vaccination of young lambs by means of a protein fraction extracted from adult *Haemonchus contortus*. *Parasitology* 1987;94:385–397.
50. Munn E A, Smith T S, Graham M, Greenwood C A. Vaccination of Merino lambs against haemonchosis with membrane-associated proteins from the adult parasite. *Parasitology* 1993;106:63–66.
51. Munn E A, Smith T S, Graham M, Travenor A S. The potential value of integral membrane proteins in the vaccination of lambs against *Haemonchus contortus*. *International Journal for Parasitology* 1993;23:261–269.
52. Opdebeeck J P, Daly K E. Immune responses of infested and vaccinated Herford cattle to antigens of the cattle tick, *Boophilus microplus*. *Veterinary Immunology and Immunopathology* 1990;25:99–108.
53. Opdebeeck J P, Wong J Y M, Dobson C. Hereford cattle protected against *Boophilus microplus* with antigens purified by immunoaffinity chromatography form larval and adult ticks. *Immunology* 1989;67:388–393.
54. Opdebeeck J P, Wong J Y M, Jackson L A. Hereford cattle immunized and protected against *Boophilus microplus* with soluble and membrane-associated antigens from the midgut of ticks. *Parasite Immunology* 1988;10:405–410.
55. Rand K N, Moore T, Sriskantha A, Spring K. Cloning and expression of a protective antigen from the cattle tick *Boophilus microplus*. *Proceedings National Academy of Science U.S.A.* 1989;86:9657–9661.
56. Roberts F H S. Reactions of calves to infestations with the stomach worm, *Haemonchus placei* (Place, 1893) Ransom, 1911. *Australian Journal of Agriculture Research* 1957;8:740–767.
57. Ross J G. Association of detectable antibodies produced by Haemonchus spp. infections in cattle, with serum globulin fractions. *Nature* 1961;190:1019–1020.
58. Ross J G. Further observations on helminthiasis in Nigerian zebu cattle: the serology response. *British Veterinary Journal* 1962;118:66–70.
59. Ross J G. The role of the larval stages of *Haeomonchus placei* infections of cattle in immunity. *Journal of Helminthology* 1963;37:359–368.
60. Ross J G. Immunogenic activity of the larval stages of *Haeomonchus placei*. *Nature* 1963;197:1221–1222.
61. Smith W D. Protection in lambs immunized with *Haemonchus contortus* gut membrane proteins. *Research in Veterinary Science* 1993;54:94–101.
62. Smith T S, Munn E A, Graham M. Purification and evaluation of the integral membrane protein H11 as a protective antigen against *Haemonchus contortus*. *International Journal for Parasitology* 1993;23:271–280.
63. Smith W D, Smith S K. Evaluation of aspects of the protection afforded to sheep immunized with a gut membrane protein of *Haemonchus contortus*. *Research in Veterinary Science* 1993;55:1–9.
64. Smith W D, Smith S K, Murray J M. Protection studies with integral membrane fractions of *Haemonchus contortus*. *Parasite Immunology* 1994;16:231–241.
65. Soulsby E J L. *Helminths, arthropods and protozoa of domesticated animals*. 7th ed 1982; W B Saunders:233–235.
66. Stromberg B E, Corwin R M. Epizootiology of *Ostertagia ostertagi* in cow-calf production systems in the American Midwest. *Veterinary Parasitology* 1993;46:297–302.
67. Tavernor A S, Smith T S, Langford C F. Immune response of Clun Forest sheep to vaccination with membrane glycoproteins from *Haemonchus controtus*. *Parasite Immunology* 1992;14:671–675.
68. Manousis T, Ellar D. *In-Vitro Cell Developmental Biology* 1990; 26:1105–1114.
69. Kurtti, T H, Ulrike G. Munderloh G G, et al. *J. Med Entomol* 1988; 25:256–261.
70. Hobbs, D J, Fryer, S E, Duimstra, Jr et al. *J. Parasitol.* 1993; 79:913–921.
71. Kurtti, T J, Munderloh U G. 1984. "Mosquito Cell Culture" In *Advances in Cell Culture*, pp 259–302, Vol. 3.
72. Munderloh, U G, Wang Y L M, Chen C. Kurtti T J, *J. Parasitol* 1994; 80:553–543.
73. Arnon, R. (Ed.) *Synthetic Vaccines* I:93–103, CRC Press, Inc., Boca Raton, Fla., 1987.
74. Martin, E. W., Ed., *Remington's Pharmaceutical Sciences*, latest edition, Mack Publishing Co., Easton, Pa. 1988.
75. Harlow and Lane, *Antibodies, A Laboratory Manual*, Cold Spring Harbor Laboratory, Cold Spring Harbor, N.Y. 1988.
76. Baron et al. *Microb. Pathog* 7:237–247, 1989.
77. DeClercq, E. *Antiviral Res.*12:1–20, 1989.
78. Miller, P S *Biotechnology* 9:358–366, 1991.
79. Cowsert et al. *Antimicrob. Agents and Chemotherapy* 37:171–177, 1993.
80. Laemmli, *Nature*, 227:680–685, 1970.
81. McKerrow, J. H., et al. 1990. *Exp. Parasitol.* 70:134–143.
82. Gambel H. R. et al. 1996. *J. Parasitol.* 82:197–202.
83. Gambel H. R. and Mansfield, L. S., 1996. *J. Parasitol.* 62:291–305.
84. Barret, J. "Biochemistry of parasite helminths" p. 208. McMillan Publishers, Ltd., London, 1981.
85. Coyne, C. et al., 1993(a). *Am. J. Vet. Res.* 54:845–855.
86. Coyne, C. et al., 1993(b). *Am. J. Vet Res.* 54:305–314.
87. Travenor, A. S., et al., 1992. *Parasitology* 14:645–655.
88. Munn, E. A., et al., 1993. *Parasitology* 106:63–66.
89. Gambel, H. R. et al., 1980. *J. Parasitol.* 66:434–438.
90. McMichael-Phillips et al., 1995. PCT application WO 95/12671.
91. Ivens, V. R., et al., 1978. Principle parasites of domestic animals in the United States. pp. 254–255. Colleges of Agriculture and Veterinary Medicine, University of Illinois at Urbana.

What is claimed is:

1. A homogeneous population of differentiated intestinal cells obtained by in vitro cultivation of intestinal cells of a nematode which infects animal tissue.

2. A composition comprising the population of differentiated intestinal cells of claim 1 and a pharmaceutically acceptable carrier.

3. A cellular fraction obtained from the population of differentiated intestinal cells of claim 1.

4. A composition comprising the fraction of claim 3 and a pharmaceutically acceptable carrier.

5. The cellular fraction of claim 3, wherein the fraction comprises membrane associated antigens.

6. The cells of claim 1, wherein the nematode is selected from the group consisting of species of Cooperia, Oesophagostomum, Ostertagia, Haemonchus, Dirofilaria and Dictyocaulus.

7. A cell lysate obtained from the population of differentiated intestinal cells of claim 1.

8. A composition comprising the population of differentiated intestinal cells of claim 1 and a culture medium thereof.

9. A non-cellular fraction obtained from the culture medium of claim 8.

* * * * *